United States Patent [19]

Stocker

[11] 4,137,127
[45] Jan. 30, 1979

[54] PROCESS FOR THE PREPARATION OF THROMBIN-LIKE ENZYMES FROM SNAKE VENOMS

[75] Inventor: Kurt F. Stocker, Oberwil, Switzerland

[73] Assignee: Pentapharm A.G., Basel, Switzerland

[21] Appl. No.: 819,473

[22] Filed: Jul. 27, 1977

[30] Foreign Application Priority Data

Aug. 17, 1976 [CH] Switzerland ............... 10493/76

[51] Int. Cl.$^2$ ............................................. C07G 7/026
[52] U.S. Cl. ................................................. 195/66 B
[58] Field of Search .......................... 195/66 R, 66 B

[56] References Cited

U.S. PATENT DOCUMENTS 3,849,252  11/1974  Percs et al. ..................... 195/62

OTHER PUBLICATIONS

Methods in Enzymology, vol. 19, pp. 715–722 (1970).

*Primary Examiner*—Lionel M. Shapiro
*Attorney, Agent, or Firm*—Pennie & Edmonds

[57] ABSTRACT

A process for the preparation of thrombin-like proteolytic enzymes from snake venoms or fractions thereof comprising contacting the snake venom or fraction thereof with heparin insolubilized by reaction with a water-insoluble carrier in order to bind the thrombin-like enzyme to the insolubilized heparin, removing the undesirable accompanying substances of the snake venom and splitting the thrombin-like enzyme from the insolubilized heparin.

15 Claims, 1 Drawing Figure

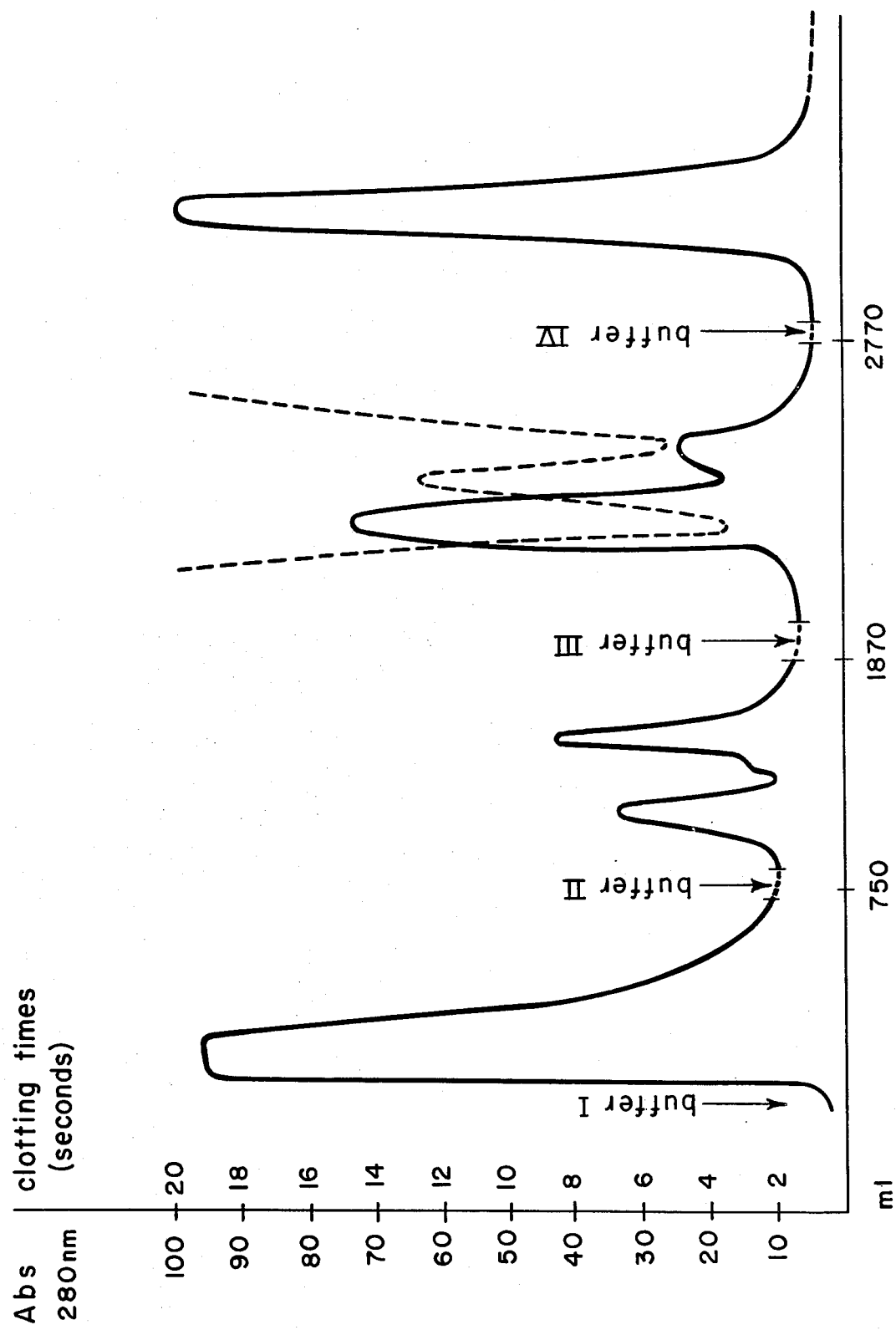

PROCESS FOR THE PREPARATION OF THROMBIN-LIKE ENZYMES FROM SNAKE VENOMS

BACKGROUND OF THE INVENTION

The invention relates to a process for preparing thrombin-like proteolytic enzymes from venoms of snakes, particularly snakes of the family Crotalidae, especially of the genera Agkistrodon, Bothrops, Crotalus and Trimeresurus.

Thrombin-like proteolytic enzymes are proteases which are obtained for instance from certain snake venoms and which, like thrombin, split fibrinopeptide A and/or fibrinopeptide B from fibrinogen, but which, unlike thrombin, have a high substrate specificity [cf. e.g. D. L. Aronson, Thrombos. Haemostas. (Stuttg.), 1976, 36, pages 9 to 13, and 1976, 35, page 477].

Thrombin-like snake venom enzymes are used as reagents for investigating blood coagulation processes, as antihaemorrhagic drugs and as agents for the experimental and therapeutic defibrinogenation and, hence, anticoagulation.

The following Table comprises indications relating to the use of thrombin-like enzymes from the venoms of some snake species and the respective literature references.

TABLE 1

| Venom from the species: | Use for: | Literature: |
|---|---|---|
| Agkistrodon contortrix | blood tests | R.M. Herzig, O.D. Ratnoff + Y.R. Shainoff: Studies on a procoagulant fraction of southern copperhead snake venom: The preferential release of fibrinoipeptide B. J. Lab. and Clin. Med. 76, 451–465 (1970) |
| Agkistrodon rhodostoma | defibrinogenation | A.A. Sharp, B.A. Warren, A.M. Paxton + M.J. Allington: Anticoagulant therapy with a purified fraction from Malayan pit viper venom. Lancet I, 493–499 (1968) |
| Bothrops atrox | defibrinogenation | N. Egberg: Experimental and clinical studies on the thrombin-like enzyme from the venom of Bothrops atrox. On the primary structure of fragment E. Acta phys. scand. Suppl. 400 (1973) |
| | haemostasis | E. Berger, A.J. Laurent + K.F. Stocker: The prophylactic and therapeutic use of Reptilase. Praxis 57, No. 17, 611–616 (1968) |
| | Blood tests | C. Funk, J. Gmur, R. Herold + P.W. Straub: Reptilase-R. A new reagent in blood coagulation. Brit. J. Haematol. 21, 43–52 (1971) |
| Bothrops jararaca | haemostasis | C. Mauro: Sulla azione emocoagulante del veleno di Bothrops jararaca. Giorn.Ital. di Chirurgia 8, 448 (1949) |
| Crotalus adamanteus | defibrinogenation | F.S. Markland + P.S. Damus: Purification and properties from the venom of Crotalus adamanteus. J. Biol. Chem. 246, 6460–6473 (1971) |
| Trimeresurus gramineus | defibrinogenation | C. Ouyang + F.Y. Yang: Purification and properties of the thrombin-like enzyme from Trimeresurus gramineus venom. Biochim. et Biophys. Acta |

TABLE 1-continued

| Venom from the species: | Use for: | Literature: |
|---|---|---|
| | | 351, 345–363 (1974). |

The said proteolytic enzymes are glycopeptides having molecular weights comprised between 18,000 and 55,000. Since they are inhibited by di-isopropyl fluorophosphate, they have to be classified in the serine protease group. Like thrombin, the thrombin-like snake venom enzymes cause the conversion of fibrinogen into fibrin by the release of fibrinopeptides; however, they differ from thrombin in their behaviour towards other blood coagulation factors and thrombocytes, and, more particularly, by the fact that their coagulating activity on plasma is not significantly inhibited by thrombin inhibitors such as heparin, hirudin, antithrombin III and heparinoids [cf. D. L. Aronson, Thrombos. Haemostas. (Stuttg.), 1976, 36, pages 9 to 13].

In order to concentrate the thrombin-like enzymes from snake venoms which generally consist of mixtures of more than 20 different pharmacologically active polypeptides, DEUTSCH (cf. E. Deutsch, "Blutgerinnungsfaktoren," Verlag Deuticke, Vienna 1955) precipitated impurities from dissolved crude venom by the action of acids and heat and recovered the thrombin-like enzymes as an enriched fraction from the remaining liquid phase by precipitation with solvents or salts. BANERJEE et al. have described the thirty-fold concentration of the thrombin-like enzyme from venom of Bothrops jararaca by ammonium sulfate precipitation from a 0.5% solution of crude venom, heat treatment of the dissolved precipitate at 65° C., separation of the precipitated impurities by centrifugation, absorption of the thrombin-like enzyme on calcium phosphate gel, elution with sodium phosphate buffer at pH 7.2, repeated fractional ammonium sulfate precipitation and finally dialysis against veronal buffer [cf. E. Banerjee, A. Devi + N. Sarkar: Isolation and purification of a coagulant from snake venom of the species Bothrops jararaca and the study of its properties, Thromb. Diath. Haem. 5, 296–303 (1960)]. British patent specifications 1,094,301 and 1,177,506 disclose the preparation of the thrombin-like enzyme from the venom of Agkistrodon rhodostoma by chromatography on triethylaminoethylcellulose and subsequent purification by gel chromatography. Thus, 2 g of crude Agkistrodon rhodostoma venom are subjected to chromatography first on a TEAE-cellulose column of 35 × 3.9 cm (= 417 ml) and then on a "Sephadex G-100" column of 97 ×6 cm (= 2826 ml). BONILLA [Thromb. Res. 6, 151–169 (1975)] describes the isolation of the thrombin -like enzyme from the venom of Crotalus horridus by chromatography of 20 g of crude venom on a column of 1766 ml of "Sephadex G-100," subsequent chromatography of the active fraction on a column of 883 ml of diaminoethylcellulose, a further chromatography on 883 ml of carboxymethylcellulose and a last purification by chromatography on a DEAE-cellulose column of 2.5 × 36 cm (176 ml) using a linearly increasing buffer concentration gradient and subsequent chromatography on a "Sephadex G-200" column of 2.5 × 33 cm. While the methods based on ion exchange and gel chromatography allow a much higher purity to be obtained than the first described adsorption method, they are time-consuming and uneconomic since relatively large columns have to be used for the chromatography of only small quantities of crude venom. Furthermore, the active eluate contains a relatively small quantity of enzyme in a large volume of liquid and, therefore, has to be concentrated either by ultrafiltration or vacuum distillation. According to U.S. Pat. No. 3,849,252 the thrombin-like enzyme from Bothrops atrox venom is obtained by precipitating impurities from 20 g of crude venom by acidification, then precipitating the enzyme by formation of a sparingly soluble complex with phenol or a phenol derivative, decomposing the said complex, subjecting the enzyme thus concentrated to a chromatography on a column of 200 ml of DEAE-Sephadex and thereafter purifying the product on a "Sephadex G-100" column of 1.8 × 92 cm (233 ml). Due to the precipitation of the thrombin-like enzyme as a complex with phenol or a phenol derivative the output of the chromatographic purification steps of this method is substantially higher than in the direct chromatography of the crude venom; however, the numerous steps of this method require a considerable expenditure of work and yield a product which has an insufficient purity and which forms with prothrombin-free plasma in the presence of calcium ions a clot insoluble in monochloroacetic acid and thus activates factor XIII. HOLLEMANN and WEISS [J. Biol. Chem. 251, 1663–1669 (1976)] achieved the isolation and purification of thrombin-like enzyme from Bothrops atrox venom by affinity chromatography of 2 g of crude venom on a 2.5 × 56 cm column (274 ml) of p-aminobenzamidinsuccinyl-diaminodi-propylaminoagarose at 4° C. using 0.15 mole of benzamidine in a sodium citrate/NaCl buffer having a pH of 9.0 and subsequent removal of the benzamidine from the eluate by dialysis. In this manner they obtained a product which did not activate factor VIII. This method, although yielding a product of sufficient purity in a few steps only, requires a relatively large column of an adsorbent which is difficult to prepare and, moreover, necessitates the use, as an elution agent, of benzamidine which, owing to its property to absorb ultraviolet light, prevents the UV-photometric control of the course of the chromatography and which, since it has a considerable toxicity, must be completely removed from the eluates, thus requiring a time-consuming dialysis.

It was now found that thrombin-like enzymes from snake venoms, although their clotting activity is not inhibited by heparin under the usual conditions of pH, ionic strength and temperature normally used in blood clotting tests, quite unexpectedly have a pronounced affinity for heparin which has been insolubilized by fixation on an insoluble carrier and can, therefore, be isolated from crude snake venoms or fractions thereof and purified by affinity chromatography on insolubilized heparin.

BRIEF SUMMARY OF THE INVENTION

The invention relates to a process for isolating thrombin-like proteolytic enzymes from snake venoms or fractions thereof which comprises contacting the snake venom or fraction thereof in an aqueous medium with insolubilized heparin fixed on a water-insoluble carrier in order to bind the thrombin-like enzyme to the insolubilized heparin, removing the undesirable accompanying substances of the snake venom and splitting the thrombin-like enzyme from the insolubilized heparin in an aqueous medium.

DETAILED DESCRIPTION OF THE INVENTION

Starting materials which can be used for carrying out the process of the invention include clearly filtered or centrifuged aqueous solutions of the crude venom of snakes of the family Crotalidae, particularly the genera Agkistrodon, Bothrops, Crotalus and Trimeresurus. Clearly filtered or centrifuged snake venom fractions in which the thrombin-like enzyme is present in enriched form and from which undesirable ballast materials have been removed by acid or heat precipitation can also be used as starting materials. Furthermore, suitable starting materials also include crude preparations of the thrombin-like enzymes which have been obtained, for instance, by precipitation with phenol or a phenol derivative from crude venom according to the process disclosed in U.S. Pat. No. 3,849,252.

Insolubilized heparin can be obtained by reacting heparin through its amino groups with the reactive groups of a polymeric water-insoluble carrier substance according to known methods and thus fixing covalently the heparin on the carrier. Insolubilized heparin can be prepared, for instance, by a method described by SCHMER and comprising binding heparin to agarose according to the cyanogen bromide method, to putrescine agarose according to the thiophosgen method or to epsilonaminocaproyl-agarose according to the carbodiimide method [cf. G. Schmer: The biological activity of covalently immobilized heparin, Trans. Am. Soc. Artificial Int. Org. 18, 321–323 (1972)]. Cellulose and the corresponding derivatives, i.e. putrescine cellulose and epsilonaminocaproyl-cellulose, can also be used as the carrier substance. Insolubilized heparin can also advantageously be prepared by reacting heparin with beads of standard size of commercially available crosslinked cyanogen bromide agarose (e.g. CNBr-Sepharose 4B sold by AB Pharmacia, Uppsala, Sweden).

The treatment of the starting material with insolubilized heparin (i.e. the binding of the thrombin-like snake venom enzyme to heparin) and the splitting of the enzyme from the insolubilized heparin can be carried out batchwise by stirring the starting material dissolved in water, an aqueous buffer solution, an aqueous electrolyte solution having no or at most a weak buffer activity or an aqueous solution containing a buffer as well as a neutral salt, e.g. sodium chloride, with the affinity adsorbent (i.e. the insolubilized heparin) and subsequent filtration, or, preferably, by affinity chromatography on a column. Suitable electrolytes include inorganic and organic salts, e.g. sodium chloride, ammonium chloride, magnesium chloride, magnesium sulfate, ammonium sulfate, calcium chloride, ammonium bicarbonate, ammonium formate, sodium acetate or triethylamine hydrochloride; or organic acids, e.g. acetic acid, tartaric acid or citric acid; or bases, e.g. ammonium hydroxide, trimethylamine or triethylamine. In the affinity chromatography the insolubilized heparin is charged onto a column the diameter of which corresponds to about one tenth of its height and equilibrated with the same aqueous medium as is used for dissolving the starting material. The outlet of the column is advantageously connected with a flow photometer which measures and automatically records the optical density of the effluent eluates at a suitable wave length (usually 280 or 254 nm). The eluates are preferably subdivided into fractions and collected by means of an automatic fraction collector.

The affinity chromatography can be carried out in detail as follows: The starting material (crude snake venom or a fraction thereof) is dissolved in water, an aqueous buffer solution, an aqueous electrolyte solution, e.g. sodium chloride solution, or an aqueous solution containing a buffer as well as a neutral salt, e.g. sodium chloride. The solution is filtered or centrifuged until it is clear and then charged onto the chromatographic column. The column is washed with the same aqueous medium as is used for dissolving the starting material until no more UV-absorbing substances are detectable in the effluent eluate. Thereafter, the column is washed with an aqueous elution agent, e.g. a buffer solution, an electrolyte solution or a solution containing a buffer as well as a neutral salt, e.g. sodium chloride, the concentration of which is higher than that of the aqueous medium in which the starting material was dissolved, in order to split the thrombin-like snake venom enzyme from the insolubilized heparin. The washing is continued until no more UV-absorbing material is eluted. Finally the column is washed with a buffer solution, an electrolyte solution or a solution containing a buffer as well as a neutral salt, e.g. sodium chloride, having a sufficiently high concentration for also completely removing substances which are bound more strongly to the insolubilized heparin than the thrombin-like enzymes in order to regenerate the affinity adsorbent after equilibration with the same equilibrating agent and to make it ready for a new working cycle.

Suitable buffer solutions include aqueous solutions of salts of inorganic or organic bases with inorganic or organic acids, or salts of amphoteric compounds with inorganic or organic acids or bases which develop a buffer activity within a pH range of 4 to 10. It is particularly advantageous to use non-toxic compounds or mixtures of compounds which contain no aromatic groups and thus do not absorb light of a wave length of 280 or 254 nm and do not disturb the UV-photometric control of the course of the chromatography, e.g. glycine/NaOH, acetic acid/NaOH, citric acid/NaOH, triethanolamine/HCl, lysine/HCl, glycylglycine/HCl and sodium phosphate buffers as well as vacuum-volatile buffer systems such as ammonium formate, ammonium/acetate and ethylenediamine tetraacetate buffers. When operating batchwise, sodium hydrogencarbonate and ammonium hydrogencarbonate buffers can also be used. Because of $CO_2$ evolution the latter are not suitable for the chromatographic operation. The thrombin-like enzymes of different snake venoms have differing affinities for insolubilized heparin bound to an insoluble carrier. Consequently, the composition of the buffer has to be adapted to the biological origin of the enzymes to be isolated. The lower the concentration of the buffer solution, the electrolyte solution or the solution containing a buffer as well as a neutral salt, the better the enzyme is bound to insolubilized heparin. However, since at low concentrations the unspecific binding capacity of heparin for proteins is also highest, it is necessary to select concentrations at which the thrombin-like enzyme is bound whereas other proteins pass unhindered through the column. For each given venom the optimum concentration conditions can be determined by simple preliminary experiments. All thrombin-like snake venom enzymes investigated are bound at concentrations of the buffer, electrolyte or buffer/neutral salt solutions which, depending on the nature of the venom, are comprised within a molarity range from 0.01 to 0.5, and at a pH comprised between 4 and 10.

For splitting the thrombin-like snake venom enzymes from the insolubilized heparin, buffer, electrolyte or buffer/neutral salt solutions are used which have a higher concentration than the solution used for binding the enzyme to the insolubilized heparin. Preferably, the same buffer solution as that used for binding the enzyme to the insolubilized heparin is used, but its concentration is increased by the addition of a strongly dissociating neutral salt, preferably sodium chloride, so that the bound enzyme is split from the insolubilized heparin. Since some snake venoms contain other substances which also have a certain affinity for insolubilized heparin, the concentration of the solution used for elution is preferably adjusted in such a manner that the thrombin-like enzyme is split off, whereas other substances having a higher affinity remain bound to the insolubilized heparin. The removal of all thrombin-like snake venom enzymes bound to insolublized heparin is preferably carried out at concentrations between 0.1 and 2 moles and at a pH comprised within the range of 4 to 10. The complete removal of all the venom constituents bound to the insolubilized heparin and having an affinity for heparin which is stronger than that of the thrombin-like enzymes is conveniently effected by means of buffer solutions, electrolyte solutions or buffer/neutral salt solutions having a pH of 4 to 10 and a molarity of 0.5 to 2. Preferably, the first buffer solution used for binding the enzyme to the insolubilized heparin is adjusted to the desired concentration by the addition of a neutral salt, preferably sodium chloride. The affinity adsorbent can be made ready for repeated use by washing it with the first buffer solution used for binding the enzyme to the insolubilized heparin.

The affinity of the insolubilized heparin for the thrombin-like snake venom enzymes is highest at low temperatures and decreases with increasing temperatures. This phenomenon can be taken advantage of for effecting the binding of the enzyme to the insolubilized heparin at low temperatures, e.g. in a column cooled with ice water, and the splitting off of the enzyme at higher temperatures by increasing the temperature in the cooling or heating jacket of the column, e.g. to 40° C., while using one and the same buffer solution having a constant concentration and pH.

The removal of the enzyme from the insolubilized heparin can furthermore be carried out at a constant buffer and/or neutral salt concentration of the aqueous medium by increasing or reducing the pH above or below, respectively, the value at which the binding of the enzyme to the insolubilized heparin took place. The pH range suitable for a given enzyme can be determined by simple preliminary experiments.

The quantity of the thrombin-like snake venom enzyme present in the eluates obtained by column chromatography can be determined by a clotting test, preferably on fibrinogen. As an example, a suitable clotting test consists in measuring the clotting time in seconds after the addition of 0.2 ml of diluted eluate to 0.2 ml of 0.4% bovine fibrinogen at pH 7.4 and 37° C. The simple determination of the clotting time is well suited for establishing an activity profile in chromatographic elution curves (see FIG. 1 of the attached drawing). From a reference curve established by the same technique using a standard thrombin preparation (e.g. U.S. standard thrombin, National Institute of Health, Bethesda, Md.), or a standard preparation of the thrombin-like snake venom enzyme concerned (e.g. Ancrod standard of the World Health Organization, or Batroxobin moojeni standard, First British Standard), the activity can be read quantitatively in NIH thrombin units, Ancrod units or Batroxobin units from the clotting time. The thrombin-like enzyme content can also be determined in enzyme units in a photometric test using a synthetic chromogenic thrombin substrate such as tosyl-Gly-Pro-Arg-p-nitroanilide hydrochloride. One unit (U) is then the quantity of enzyme which splits 1 μmole of substrate in one minute under test conditions.

From the combined active fractions undesired buffer substances and salts can be removed completely or partially by dialysis. The simultaneous desalting and concentration of the combined active fractions can be effected by ultrafiltration, e.g. on a "Diaflo" membrane UM-2 (Amicon, Oosterhout, Holland). Whether the fraction containing the thrombin-like snake venom enzyme should be desalted and concentrated or not depends on the type of the buffer used, the quantity of chromatographed product and the intended application of the product. If non-toxic buffer systems, e.g. glycine/NaOH/NaCl, are used in the preparation of thrombin-like enzyme products to be used for experimental and/or therapeutic defibrinogenation, the product has not to be or has to be only partially desalted in order that an isotonic sterile, pyrogen-free solution can be prepared from the combined active fractions according to conventional methods. Partial desalting is also sufficient when the thrombin-like snake venom enzyme present in an eluate has to be further purified by chromatography. In this case, it is sufficient to reduce the buffer or salt concentration of the eluate to the lower value required for the affinity bonding in order to bind again the enzyme to the insolubilized heparin.

The nature of the bonding between the insolubilized heparin and the thrombin-like enzymes has not been clearly elucidated. It can be assumed that this bonding is similar to the chemical bonding which takes place between enzymes and substrates as well as between enzymes and inhibitors in the reversible inhibition (cf. S. M. Rapoport: "Medizinische Biochemie," VEB Verlag Volk und Gesundheit, Berlin, 1975, p. 133–155).

The process of the invention possesses several substantial advantages over the known processes for the preparation of thrombin-like snake venom enzymes. The binding capacity of insolubilized heparin for thrombin-like snake venom enzymes is so high that a chromatography column having a volume of 20 ml only is sufficient for partitioning 4 g of crude venom or an equivalent quantity of a venom fraction after a preliminary purification whereby thrombin-like enzymes having a high degree of purity are obtained. This corresponds to forty times the capacity of an ion exchange chromatography on cellulose exchangers, about 400 times the capacity of a gel chromatography and about 25 times the capacity of the affinity chromatography on p-aminobenzamidine-succinyl-diaminodipropylamino-agarose. This high binding capacity of insolubilized heparin not only increases the partition capacity of a relatively small chromatography apparatus but also causes the enzyme to be present in the active fractions of the eluate in considerably higher concentrations than is the case in ion exchange and gel chromatography so that much less expenditure of work is required for concentrating and desalting the eluates. The process of the invention allows the thrombin-like snake venom enzymes to be obtained in a few working steps which are easy to perform, automatable to a large extent and well recordable. The use of toxic elution agents is superfluous.

It was quite unpredictable that thrombin-like enzymes could be isolated from snake venoms by binding them to insolubilized heparin. Admittedly it was known to purify thrombin by affinity chromatography on heparin previously insolubilized by fixation on Sepharose [cf. I. Danishefsky et al., Thrombosis Research 8, 134 (1976)]. This method makes use of the fact that heparin inhibits thrombin, i.e. has a high affinity or binding capacity for thrombin. The discovery of the fact that thrombin-like proteolytic snake venom enzymes, which as such are not inhibited by heparin, i.e. show no noticeable affinity or binding capacity with regard to dissolved heparin, or, in other words, are not bound by dissolved heparin, could be bound by insolubilized heparin and thus be isolated and purified by affinity chromatography on insolubilized heparin was very surprising and unexpected.

The invention is further illustrated by the following examples which, however, are not intended to limit the scope of the invention.

EXAMPLE 1

9 g of sodium heparin having a specific biological activity of 162 international units per mg were dissolved in 1 liter of 0.1 M sodium bicarbonate buffer containing 0.5 mole of sodium chloride per liter and having a pH of 8.3. To the solution were added 45 g of CNBr-Sepharose 4B (AB Pharmacia, Uppsala, Sweden) previously soaked and washed in 0.001 N hydrochloric acid. The mixture was stirred for 2 hours. After termination of the reaction the mixture was filtered on a glass suction filter G-3, and the separated Sepharose-heparin was washed five times with portions of 300 ml of sodium bicarbonate buffer having the above mentioned composition. In order to saturate possibly still remaining reactive CNBr groups the Sepharose-heparin was stirred for 2 hours with 1 liter of 0.5% ethanolamine in the sodium bicarbonate buffer of the above mentioned composition. The Sepharose-heparin was again collected on a glass suction filter and washed three more times with portions of 300 ml of sodium bicarbonate buffer. The Sepharose-heparin was then washed with 0.1 M sodium acetate buffer of pH 4.0 until the filtrate had a pH of 4.0. Finally, the insolubilized heparin was washed with several portions of 0.1 M glycine/NaOH buffer of pH 8.5, poured onto a column having a diameter of 26 mm and equilibrated with the same glycine/NaOH buffer. The column which had a height of 29 cm and thus contained about 153 ml of insolubilized heparin was arranged for descending chromatography. The outlet of the column was connected by means of a flow photometer equipped with an automatic recorder and adjusted for measuring at 280 nm (nanometer) to a fraction collector adapted for collecting fractions of 350 drops each.

30 g of venom from Bothrops atrox (*Bothrops moojeni* according to HOGE) were dissolved in 600 ml of distilled water. The pH value of the solution was adjusted to 3.0 by means of 1 N hydrochloric acid and, after an incubation time of 1 hour, to 7.3 by means of 1 N NaOH. The resulting flocculent product was separated by centrifugation and discarded. To the remaining liquid a solution of 15 g of sodium salicylate in 300 ml of distilled water was added. The pH of the solution was adjusted to 3.0 with 1 N hydrochloric acid. After 60 minutes the precipitate which had formed was separated by centrifugation, taken up in 200 ml of 0.1 M glycine/NaOH buffer at a pH of 8.5 and washed on an ultrafilter (Diaflo membrane UM-2, Amicon) with the same buffer until a sample of the filtrate, upon addition of ferric chloride, did not show a violet coloration any more and was, therefore, free of salicylic acid. The concentrate of about 30 ml on the filter was adjusted to a volume of 50 ml by the addition of 0.1 M glycine/NaOH buffer adjusted to a pH of 8.5. It then had a content of 2240 Batroxobin units (BU) per ml and was poured onto the prepared Sepharose-heparin column. Ballast materials were eluted by rinsing with 750 ml of 0.1 M glycine/NaOH buffer of pH 8.5 (buffer I). Thereafter, the column was washed with 0.1 M glycine/NaOH buffer containing 0.1 mole of sodium chloride per liter and having a pH of 8.5 (buffer II) until 1120 ml of liquid had flown through the column whereby again ballast materials were eluted. Then, the thrombin-like enzyme was collected in the form of two UV-absorbing and fibrinogen-coagulating zones by elution with 0.1 M glycine/NaOH buffer containing 0.25 mole of sodium chloride per liter and having a pH of 8.5 (buffer III) up to a flow volume of 900 ml. Finally, the substances which had remained bound to the Sepharose-heparin were removed by elution with 600 ml of glycine/NaOH buffer containing 1 mole of sodium chloride per liter and having a pH of 8.5 (buffer IV). The course of the chromatography is shown schematically in FIG. 1 of the attached drawing.

FIG. 1 is a diagram in which, on the one hand, the UV-absorption (Abs) at 280 nanometer and, on the other hand, the fibrinogen clotting times in seconds obtained with the eluate samples at a dilution of 1:10 are plotted as functions of the collected liquid volumes in ml. The absorption is represented by the continuous curve while the clotting activity is represented by the dotted profile. The condensed representation of the liquid volumes is indicated by the dotted interruptions in the absorption curve.

The thrombin-like enzyme (Batroxobin) was present in 800 ml of eluate at a concentration of 100 Batroxobin units per ml. Thus, the yield amounted to 7.4%, based on the starting 112,000 Batroxobin units. The eluate was concentrated to 80 ml on an ultrafilter (Diaflo membrane UM-2, Amicon) and was then used as a Batroxobin concentrate for the preparation of a pharmaceutical product with a Batroxobin content of 22 Batroxobin units per ml for the therapeutic defibrinogenation.

EXAMPLE 2

0.1 g of venom from the snake species *Agkistrodon contortrix* was dissolved in 1.5 ml of aqueous 0.1 M glycine/NaOH buffer having a pH of 6.0. The solution was poured onto a 17 × 70 mm (16 ml) column of Sepharose-heparin. The column was washed with the same buffer until the effluent washing liquid showed no more light absorption at 280 nm. Then, the column was rinsed with 0.1 M glycine buffer containing 0.75 mole of sodium chloride per liter and having a pH of 6.0 until no more UV-absorbing material was washed out from the column. This eluate which contained ballast material was discarded. Thereafter, the thrombin-like enzyme was isolated by elution with 0.1 M glycine buffer containing 1.0 mole of sodium chloride per liter and having a pH of 6.0. There were obtained 22 ml of eluate having a clotting activity on fibrinogen. Measured on the synthetic chromogenic substrate benzoyl-Pro-Phe-Arg-p-nitroanilide hydrochloride, the activity amounted to a total of 6996 mU (milliunits). The total protein content of the active eluate amounted to 6.2 mg. The thrombin-like enzyme from *Agkistrodon contortrix* venom purified in the manner described above showed only one zone in the electrophoresis on polyacrylamide gel in the presence of sodium dodecylsulfate and proved to be free of fibrinolytic activity in the test on the unheated fibrin plate (cf. P. Brakman and T. Astrup in Thrombosis and Bleeding Disorders, editors: N. U. Bang, F. K. Beller, E. Deutsch and E. Mammen, Thieme and Academic Press, Stuttgart, New York, London, 1971, p. 332). The eluate was concentrated to 1–2 ml on an ultrafilter (Diaflo membrane UM-2, Amicon, Oosterhout, Holland). The concentrate was mixed with 150 mg of lactose, diluted to 30 ml with distilled water, filled into vials of 1.0 ml and freeze-dried. There were thus obtained 30 vials containing each 200 mU of enzyme in a stable, immediately soluble form. In this form the product can be used for investigating the conversion of fibrinogen into fibrin under physiological and pathological conditions.

EXAMPLE 3

0.1 g of venom from the snake species Agkistrodon rhodostoma (10,500 Ancrod units) was dissolved in 1.5 ml of aqueous 0.01 M glycine buffer having a pH of 6.0. The solution was poured onto a 17 × 70 mm (16 ml) column of Sepharose-heparin equilibrated with the same buffer. The column was washed with the same buffer solution until no more UV-absorbing material was detected in the eluate by the flow photometer. Then, the column was washed with 0.01 M glycine buffer containing 0.1 mole of sodium chloride per liter and having a pH of 6.0 in order to remove ballast material. Finally, the thrombin-like enzyme (Ancrod) was eluted with 0.01 M glycine buffer containing 0.25 mole of sodium chloride per liter and having a pH of 6.0. There were obtained 120 ml of a solution containing 27 Ancrod units per ml. This product showed only one zone in the electrophoresis on polyacrylamide gel in the presence of sodium dodecylsulfate.

What I claim is:

1. A process for preparing thrombin-like proteolytic enzymes from snake venoms or fractions thereof which comprises contacting the said snake venom or fraction thereof in an aqueous medium with insolubilized heparin bound to a water-insoluble carrier in order to bind the thrombin-like enzyme to the insolubilized heparin, removing undesirable accompanying substances of the snake venom and splitting the thrombin-like enzyme from the insolubilized heparin in an aqueous medium.

2. The process according to claim 1 in which water is used as the aqueous medium for binding the enzyme to the insolubilized heparin.

3. The process according to claim 1 in which the aqueous medium used for binding the enzyme to the insolubilized heparin is a 0.01 to 0.5 M buffer solution having a pH of 4 to 10.

4. The process according to claim 1 in which the aqueous medium used for binding the enzyme to the insolubilized heparin is an aqueous 0.01 to 0.5 M electrolyte solution having a pH of 4 to 10 and having no or at most a weak buffer activity.

5. The process according to claim 4 in which an aqueous solution of sodium chloride is used as the electrolyte solution.

6. The process according to claim 1 in which the aqueous medium used for binding the enzyme to the insolubilized haparin is an aqueous solution containing a buffer and a neutral salt and having a total concentration of 0.01 to 0.5 mole per liter and a pH of 4 to 10.

7. The process according to claim 1 in which the insolubilized heparin is a product obtained by reacting heparin through its amino groups with the reactive groups of a polymeric water-insoluble carrier substance, e.g. agarose, putrescine-agarose, epsilonaminocaproylagarose or cyanogen bromide agarose.

8. The process according to claim 1 in which the aqueous medium used for splitting the enzyme from the insolubilized heparin is an aqueous buffer solution the molar concentration of which is higher than that of the solution used for binding the enzyme to the insolubilized heparin and is comprised between 0.1 and 1 mole per liter, and which has a pH of 4 to 10.

9. The process according to claim 1 in which the buffer solution contains 0.1 to 1 mole of a neutral salt, e.g. sodium chloride, per liter and has a total concentration of 0.1 to 2 moles per liter.

10. The process according to claim 1 in which the enzyme is split from the insolubilized heparin at a temperature which is higher than the temperature at which the enzyme is bound to the insolubilized heparin.

11. The process according to claim 1 in which the enzyme is split from the insolubilized heparin by means of the same buffer solution or buffer/neutral salt solution as is used for binding the enzyme to the insolubilized heparin, but at a pH which is higher or lower than the pH at which the enzyme is bound to the insolubilized heparin.

12. The process according to claim 1 which is carried out batchwise by stirring the snake venom or fraction thereof in the aqueous medium used for binding the enzyme to heparin with the insolubilized heparin, separating the resulting reaction product by filtration and stirring the said reaction product with the aqueous medium used for splitting the enzyme from the insolubilized heparin in order to liberate the enzyme.

13. The process according to claim 1 which is carried out by chromatography by placing a solution of the snake venom or a fraction thereof in the aqueous medium used for binding the enzyme to heparin on a column of insolubilized heparin, eluting the undesirable accompanying substances of the snake venom and washing the column with the aqueous medium used for splitting the enzyme from the insolubilized heparin in order to split the enzyme from the insolubilized heparin and removing it from the column.

14. The process according to claim 1 in which the removal of the undesirable accompanying substances is carried out by elution of the same on the one hand by means of the aqueous medium used for binding the enzyme to the insolubilized heparin and on the other hand by means of a buffer and/or electrolyte solution the concentration of which is higher than that of the aqueous medium used for binding the enzyme to the insolubilized heparin, but lower than that of the aqueous medium used for splitting the enzyme from the insolubilized heparin.

15. The process according to claim 8 in which the buffer solution contains 0.1 to 1 mole of a neutral salt, i.e. sodium chloride, per liter and has a total concentration of 0.1 to 2 moles per liter.

* * * * *

UNITED STATES PATENT AND TRADEMARK OFFICE
CERTIFICATE OF CORRECTION

PATENT NO. : 4,137,127
DATED : January 30, 1979
INVENTOR(S) : Kurt F. Stocker

It is certified that error appears in the above-identified patent and that said Letters Patent are hereby corrected as shown below:

Column 1, line 36, reads "fibrinoipeptide", should read --fibrinopeptide--

Column 1, line 61, Table I, after "properties" should follow --of a thrombin-like enzyme--

Column 2, line 35, reads "absorption", should read --adsorption--

Column 3, line 35, reads "VIII", should read --XIII--

Column 9, line 41, reads "7.4%", should read --71.4%--

Signed and Sealed this

Ninth Day of October 1979

[SEAL]

Attest:

RUTH C. MASON
Attesting Officer

LUTRELLE F. PARKER
Acting Commissioner of Patents and Trademarks